United States Patent [19]

Asakura et al.

[11] Patent Number: 4,723,439
[45] Date of Patent: Feb. 9, 1988

[54] HUMIDITY DETECTOR

[75] Inventors: Masahiro Asakura; Tetsuya Sakamoto, both of Kami, Japan

[73] Assignee: Kurabe Industrial Co., Ltd., Shizuoka, Japan

[21] Appl. No.: 927,491

[22] Filed: Nov. 5, 1986

[30] Foreign Application Priority Data

Jan. 31, 1986 [JP] Japan .................................. 61-13547

[51] Int. Cl.[4] ............................................ G01N 27/04
[52] U.S. Cl. ....................................... 73/29; 73/27 R; 73/336.5; 338/35
[58] Field of Search ....................... 73/29, 27 R, 336.5; 338/35

[56] References Cited

U.S. PATENT DOCUMENTS

| | | | |
|---|---|---|---|
| 3,478,574 | 11/1969 | Modell | 73/27 R |
| 3,564,474 | 2/1971 | Firth et al. | 73/27 R |
| 3,959,764 | 5/1976 | Allman | 73/27 R |
| 4,036,592 | 7/1977 | Brown et al. | 73/27 R |

FOREIGN PATENT DOCUMENTS

| | | | |
|---|---|---|---|
| 49847 | 3/1982 | Japan | 73/29 |
| 167650 | 2/1965 | U.S.S.R. | 73/336.5 |

Primary Examiner—Stewart J. Levy
Assistant Examiner—Joseph W. Roskos
Attorney, Agent, or Firm—Spencer & Frank

[57] ABSTRACT

A humidity detector which is disclosed herein includes a humidity sensing element consisting of a heating resistance wire coil and a humidity sensing portion of a metal oxide or metal oxides sintered on the coil with the opposite ends of the coil being exposed, a heating circuit for energizing the coil to increase the temperature of the humidity sensing portion to a level higher than the temperature in a measuring atmosphere, and a resistance variation detecting circuit for detecting the variation in resistance between the opposite ends of the coil depending upon the humidity contained in the measuring atmosphere. The metal oxide may be Al2O3 or a mixture of Al2O3 with at least one selected from the group consisting of SnO2, ZnO, TiO2 and MgO.

7 Claims, 5 Drawing Figures

HUMIDITY DETECTOR

BACKGROUND OF THE INVENTION

The present invention relates to a humidity detector using a humidity detecting element having a humidity sensing portion formed by sintering a metal oxide or metal oxides on a heat resistant wire coil.

There is well known a method for measuring the humidity in air, which utilizes the principle that the heat conductivity in a space varies depending upon the quantity of water vapor contained in the space, for example, as disclosed in U.S. Pat. No. 1,855,774.

The above method is realized by the construction made by the incorporation, in a bridge circuit, of a detecting element disposed in a measuring atmosphere in many cases and a reference element disposed in a space of the known humidity and having the same temperature-resistance characteristic as the detecting element.

A thermistor and a platinum wire are utilized as a detecting element.

A method as described in U.S. Pat. No. 4,419,888 is based on the aforementioned principle. This method involves supplying an electric current to a detecting element disposed in a measuring atmosphere and having a temperature characteristics found in a thermistor or the like to heat the detecting element to a temperature higher than that of such atmosphere. The resistance value of the detecting element is varied depending upon the quantity of water vapor contained in the above atmosphere, and this variation is detected. Then, the humidity in such atmosphere is detected from such variation.

There is also known a solid state thermal conductive gas detecting method which employs an element made by applying an n-type semiconductor such as $SnO_2$ and ZnO onto a platinum wire, as disclosed in Japanese Patent Publication No. 34640/79. In such a detecting device, when an electron donative gas such as a combustible gas has been adsorbed on a gas detecting portion made of a metal oxide semiconductor such as $SnO_2$, the electron concentration in the detecting portion increases, and with the increase in electric conductivity, the increase in electron concentration promotes an increase in heat conductivity. As a result, the two actions reducing the temperature of the detecting portion cause the resistance of the platinum wire coil disposed at the center of the detecting portion to be reduced, thus detecting the concentration of the gas which is to be detected.

However, the conventional devices are accompanied by various problems. The output of the heat conduction type humidity detecting element with platinum employed as a detecting element is substantially smaller than that of the aforementioned thermistor heat conduction type humidity detecting element. Moreover, the platinum coil detecting element is very sensitive in thermal dissipation at an operating temperature of about 200° C. and is liable to be influenced by a slight mechanical vibration and wind.

In general, if an electric current is previously supplied so that the temperature of the detecting element may reach a level higher than the atmosphere temperature, the sensitivity can be improved. However, there is a problem that when the platinum coil detecting element is brought into a higher operating temperature, the output is unstable.

In the thermistor heat conduction type himidity detection, when the thermistor is heated to 200° C. or more, it may be broken by the self-heating.

The element made by applying an n-type semiconductor on the platinum wire has a relatively high sensitivity because of the purpose of detecting a gas, but has a lower sensitivity in humidity and hence, is not suitable for use as a humidity detecting element. Further, because the temperature at which the metal oxide semiconductor has been sintered is relatively low (at 800° C. to 900° C.), the operation in a hot and humid atmosphere (e.g., at 80° C. and 95% RH) causes the generation of a micro-crack which will grow into a large crack in a short time, resulting in a substantial variation in the resistance value. This is also a serious disadvantage.

SUMMARY OF THE INVENTION

It is an object of the present invention to povide a humidity detector wherein the drawbacks found in the conventional devices are overcome.

It is another object of the present invention to provide a humidity detector which uses an operating principle different from that of the foregoing heat conduction type humidity detecting element and enables the measurement in a wider range of a lower humidity to a higher humidity, and further, which is durable to the variations in surroundings such as a mechanical vibration.

According to the present invention, the above objects are accomplished by providing a humidity detector comprising a humidity sensing element consisting of a heating resistance wire coil and a humidity sensing portion of a metal oxide or metal oxides sintered on the coil with the opposite ends of the coil being exposed, heating means for energizing the coil to increase the temperature of the humidity sensing portion to a level higher than the temperature in an atmosphere whose humidity is to be measured, and resistance variation detecting means for detecting the variation in resistance between the opposite ends of the coil depending upon the humidity contained in the atmosphere.

With such an arrangement, the bulk resistance of the humidity sensing portion formed by the sintering is reduced by the adsorption of moisture in the atmosphere when the humidity detecting element is heated to a given temperature higher than the temperature in the atmosphere. As a result, the variation in resistance between the opposite ends of the coil is detected.

The reduction in resistance value causes each molecule of water to be adsorbed on the humidity sensing portion consisting essentially of $Al_2O_3$, so that a proton dissociated in the field of a crystal particle is supplied to form an electrolyte layer, thereby providing an increase in electric conductivity of the humidity sensing portion. In short, a carrier for a charge is a cation, and a mechanism for varying the resistance is different from that in the conventionally proposed element.

The metal oxide may be $Al_2O_3$ or a mixture of $Al_2O_3$ with at least one metal oxide selected from the group consisting of $SnO_2$, ZnO, $TiO_2$ and MgO, and such metal oxide or mixed metal oxides may be sintered to the heating resistance wire coil. The operation of the humidity detector including the humidity detecting element having thus-formed humidity sensing portion may provide outputs equivalent to or over those in use of the platinum heat conduction type humidity detecting element.

Since the metal oxide or oxides is or are firmly sintered to the heating resistance wire coil at a high temperature, the stability in zero balance and output voltage against the influences of a mechanical vibration and wind is extremely good even during operation at a temperature as high as 400° C.

If the sintering has been conducted at an average temperature as extremely high as 1250° C., no microcracks can be produced in the metal oxide sintered portion even during operation in a hot and humid atmosphere, leading to an extremely high reliability.

In addition, bringing operating temperature of the humidity detecting element to a level of about 400° C. facilitates the adsorption and desorption of water vapor, an increase in response speed and a substantial reduction in hysteresis.

Further, from the fact that the operating temperature can be brought to a level of about 400° C. or more, any dirt may always be burned and hence, no particular cleaning is required, thus making it possible to conduct a repeated detection.

The above and other objects, features and advantages of the invention will become apparent from reading of the following description taken in conjunction with the accompanying drawings.

DESCRIPTION OF THE PREFERRED EMBODIMENTS

The present invention will now be described by way of the preferred embodiments with reference to the accompanying drawings.

Figure 1:
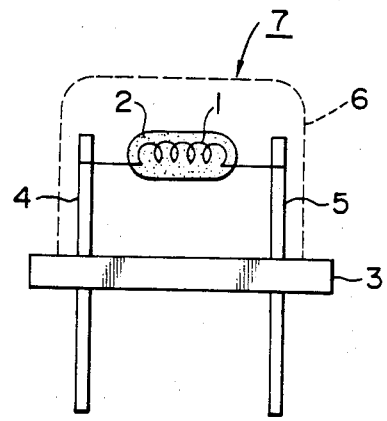
FIG. 1 is a sectional view of an embodiment of a humidity detecting element used in a humidity detector according to the present invention.

FIG. 1 is a view of an embodiment of a humidity detecting element used in a humidity detector according to the present invention. Terminal pins 4 and 5 are embedded in a stem 3 of an insulating structure to extend vertically upwardly and downwardly from the stem 3.

A platinum wire having a diameter of 0.05 mm is wound for 17 turns at a uniform pitche with a coil diameter of 0.5 mm (the coiled portion having a length of 2.5 mm) to form a heat resistance wire coil 1.

Five materials of $Al_2O_3$, $SnO_2$, ZnO, $TiO_2$, and MgO are prepared as materials for a humidity sensing portion, and one or more metal oxides of $SnO_2$, ZnO, $TiO_2$ and MgO are incorporated in $Al_2O_3$ at 12 kinds of weight ratios given in Table 1 which will be given hereinbelow, thereby giving samples. A sample of simple $Al_2O_3$ is also prepared. The respective samples as a material for the humidity sensing portion are dissolved with pure water and each is directly applied on a respective platinum coil 1. The resulting materials are air dried and then fired at a temperature of about 1,000° C. to form respective humidity sensing portions.

The contour of each humidity sensing portion is cylindrical with a diameter of 1.2 mm and a length of 3.0 mm.

The terminal pins 4 and 5 are embedded in a stem 3 of an insulating structure to extend vertically upwardly and downwardly from the stem 3.

The opposite ends of each platinum coil 1 having the humidity sensing portion formed thereon are respectively secured to the upper ends of such a pair of terminals 4 and 5 embedded in a stem 3, by electric welding. Then, each platinum coil 1 is energized so that the average temperature thereof may be maintained at 1250° C., and the metal oxide 1 is further firmly sintered.

A respective perforated cap 6 is sealingly mounted on each stem 3 to form 13 types (Nos. 1 to 13) of humidity detecting elements 7. It is to be noted that in the sample No. 13, only $Al_2O_3$ is sintered on the heat resistance coil. The sample No. 14 consists of only the heat resistance coil and prepared as corresponding to the conventional platinum wire humidity sensing element. The humidity sensing elements formed in the above manner are evaluated using a bridge circuit shown in FIG. 2.

It should be noted that this bridge circuit can be utilized as an actual humidity measuring circuit, and a device comprising a humidity detecting element according to the present invention being incorporated in such a bridge circuit forms a first embodiment of a humidity detector according to the present invention.

For this evaluation, 13 reference elements of the same kinds as those described above are likewise prepared which have been formed in the same process until the metal oxides 2 of the humidity detecting elements 7 have been firmly sintered. Each of thus formed elements is sealed by a sealing cap in dry air with a dew point of about −45° C. and the resulting element is referred to as a reference element 8.

Further, for comparison, a similar reference element is also prepared for the sample No. 14.

The humidity detecting element 7 and the reference element 18 are connected in series to a 2.0 V power source 11, and a series-circuit of resistances 9 and 10 each having a resistance value of approximately 1 KΩ and forming a bridge side is further connected. The resistances 9 and 10 are finely adjusted near 1 KΩ in accordance with the resistance value of the individual element.

An electric current of about 240 mA is supplied to the humidity detecting element and the reference element, so that each element is heated to about 400° C. At this time, the humidity detecting element 7 and the reference element 8 are thermally coupled by an heat evening plate to have the same temperature.

Figure 2:
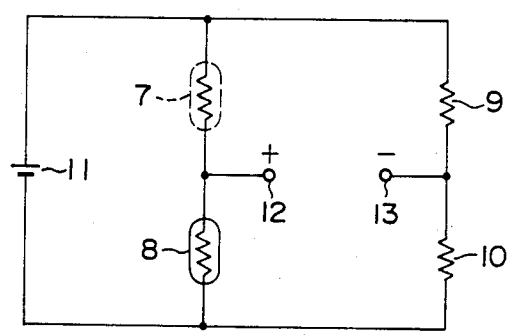
FIG. 2 is a circuit diagram illustrating an example of the humidity measurement by the humidity detecting element of the present invention and the heat resistance wire heat conduction type humidity detecting element.

In the measuring circuit shown in FIG. 2, each reference element 8 is sealed in the dry air with a dew point of about −45° C. and with a saturated absolute humidity of about 0.1 $g/m^3$ which value is considered as a standard condition. When the humidity detecting element is in such a condition, the resistance side of the bridge is adjusted so that the bridge may be balanced (have an output of zero).

Figure 3:
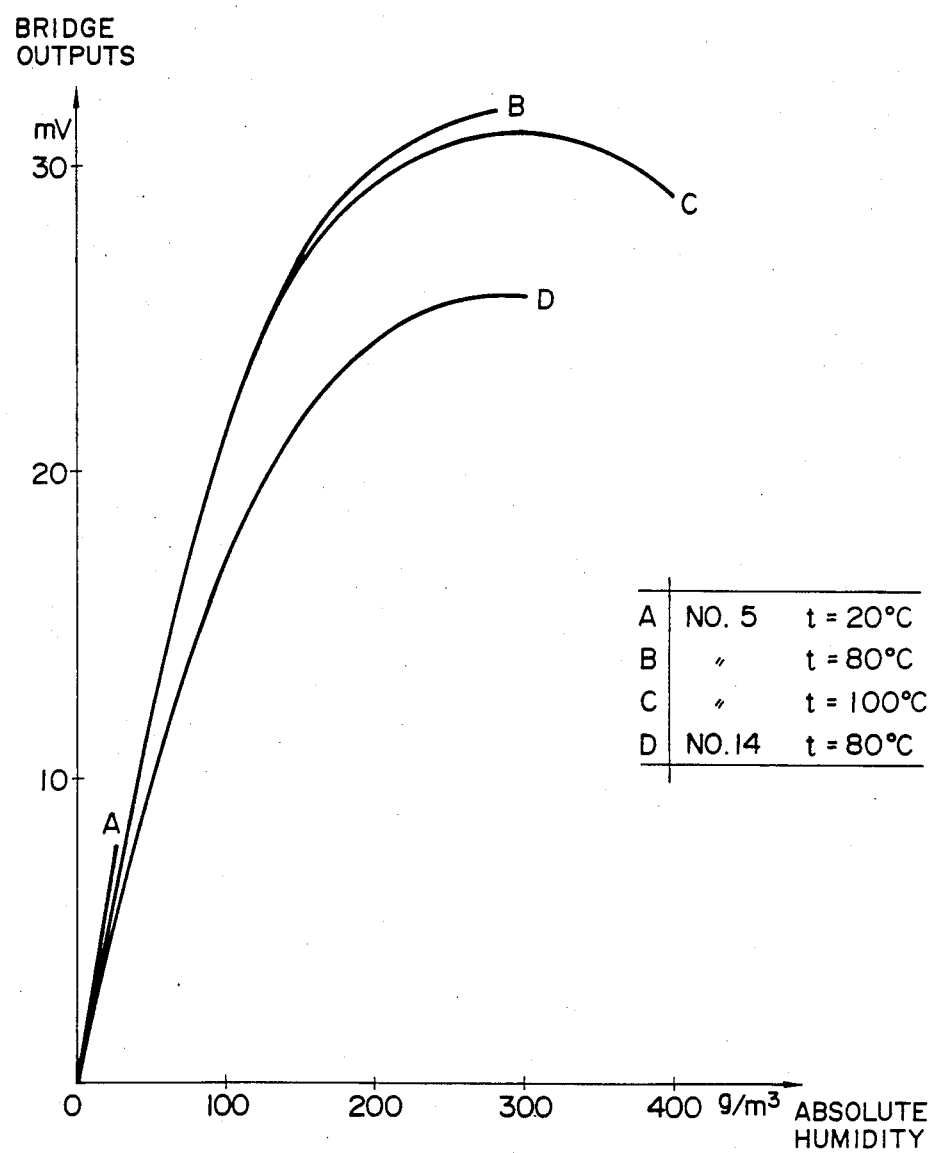
FIG. 3 is a graph illustrating the output characteristics of the humidity detecting element of the present invention and the platinum heat conduction type humidity detecting element.

In FIG. 3, there is shown an output given when a humidity detecting element using the material of the sample No. 5 ($Al_2O_3:SnO_2:MgO=2:1:1$) shown in Table 1 and the reference element are connected in the bridge circuit shown in FIG. 2, wherein curves (A), (B) and (C) indicate output voltages when the open air is at 20° C., 80° C. and 100° C., respectively.

It can be seen from FIG. 3 that the resistance value of the humidity detecting element 7 decreases with the increase in humidity. Indicated by a curve (D) in FIG. 3 is the result which has been obtained from the determination of the output characteristic, with the average temperature of the platinum coil (corresponding to the conventional humidity sensing element of platinum wire) of the sample No. 14 being increased up to about 400° C. In this case, the resistances 9 and 10 were at 1.000 KΩ and 1.051 KΩ, and the power source was at 1.7 V. The reference element 8 was sealed in the dry air with the dew point of about −45° C., and the temperature of the open air was 80° C.

As indicated by (D) in FIG. 3, if the self-heated temperature of platinum is increased to 400° C., the output is very large, and the higher humidity up to which the continuous measurement is available from the lower humidity is of about 250 $g/m^3$. This is 1.7 times the value obtained upon the operation at 200° C. However, the platinum coil heated to the substantially high temperature of 400° C. is very sensitive in thermal dissipation, so that the condition of thermal dissipation is varied under the influence of a slight mechanical vibration and a wind, resulting in a lack of stability in zero balance and output voltage of the bridge. For this reason, it is necessary with the humidity sensing element to prepare a housing case extremely difficult to be influenced by the variation in surroundings, attendant with the difficulty in reduction in size and cost.

Given in Table 1 are the bridge outputs obtained for every sample given in Table 1 under the conditions of an open air temperature of 80° C., an absolute humidity of 240 $g/m^3$ kept constant, and an operating temperature of 400° C. of the humidity sensing portion in the measuring circuit shown in FIG. 2. The samples Nos. 5 and 6 exhibit a sensitivity larger than that of the sample No. 14. Some samples have an output lower than that of the simple platinum coil (the sample No. 14), regardless of the enlargement in surface area due to the metal oxide sinters. This indicates that the humidity detecting element of the present invention is not intended to detect only the deviation in heat conductivity between the dry air and the wet air and on the contrary, the proportion in contribution to the output of electric conductivity is larger.

An examination will now be made for the reaction of the sample No. 5 to a combustible gas.

With the use of the above-described bridge circuit, the output of −35.0 mV reverse to the humidity is provided at an isobutane concentration of 2%, wherein the operating temperature is 400° C. This means that the sample No. 5 obviously presents the action of a catalyst on the combustible gas, thereby causing the contact combustion to increase the temperature of the humidity sensing portion.

The action of the metal oxide semiconductors of $SnO_2$ and $ZnO$ is ineffective on the combustible gas and effective on the humidity, which is the nature peculiar to the present invention.

After the resistances 9 and 10 are first finely adjusted in the measuring circuit shown in FIG. 2 to provide a zero balance, the drift of the zero balance due to the variation in humidity is on the order of 1 mV, thus making it possible to provide a significant temperature compensation effect.

It can be understood from the curves of the bridge outputs in FIG. 3 that the temperature dependence is also extremely small.

The measurement of the response speeds of the individual samples in the measuring circuit shown in FIG. 2 showed that the response speed is as high as 4 to 9 seconds for adsorption and 7 to 12 seconds for desorption, and the difference in output between the adsorption and desorption, i.e., a so-called hysteresis, is also extremely small.

Even in a resistance temperature detector or thermistor temperature detector having a consistent humidity coefficient and thermal dissipation constant, the temperature compensation is sufficiently available, if the reference element 8 is incorporated at a suitable point in the bridge circuit.

Figure 4:
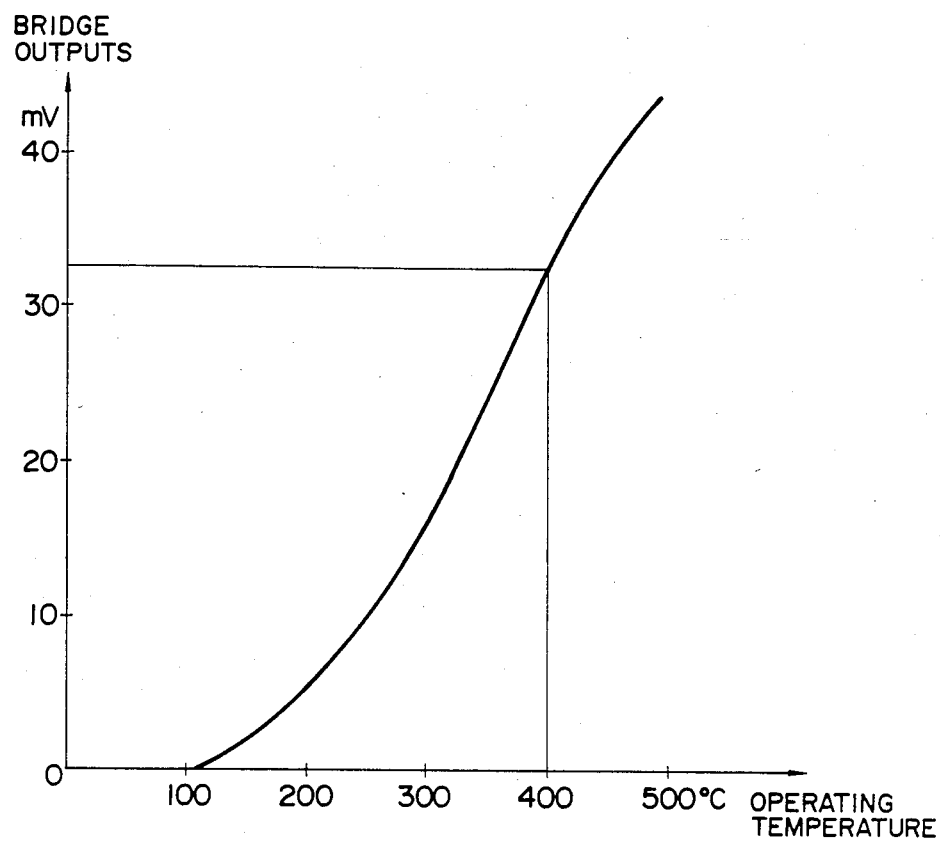
FIG. 4 is a graph illustrating the output characteristic of the humidity detecting element according to the present invention with respect to the operating temperature.

In FIG. 4, there is shown the result of the measurement for how the bridge output varies when the voltage of the power source 11 is varied and the operating temperatures of the humidity detecting element 7 and the reference element 8 are varied in the measuring circuit shown in FIG. 2. The conditions in the measuring atmosphere are at 80° C. and 240 $g/m^3$ which are kept constant, and use is made of the humidity detecting element 7 and the reference element 8 of the type defined in sample No. 5 in Table 1. It can be understood from FIG. 4 that if the operating temperature of the humidity detecting element 7 is on the order of 400° C., a sufficiently large output is provided.

The humidity detector can also be realized by the processing of information on the variation in resistance of the humidity detecting element and information on the atmospheric temperature rather than by use of the aforementioned bridge circuit.

Figure 5:
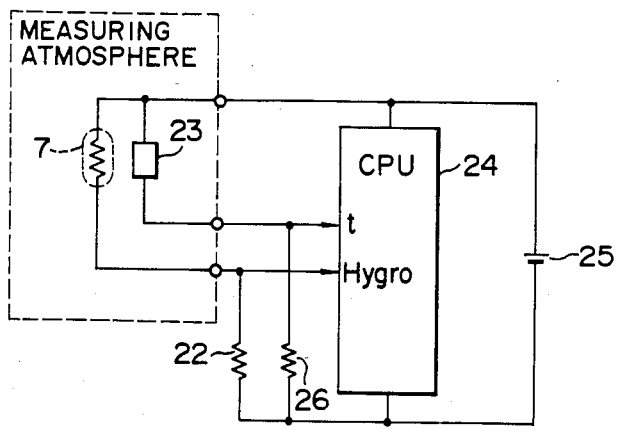
FIG. 5 is a block diagram illustrating a second embodiment of a humidity detector according to the present invention.

FIG. 5 is a block diagram illustrating a second embodiment of a humidity detector according to the present invention. The humidity detecting element 7 and a temperature sensor 23 are contained in a measuring atmosphere, that is, the atmosphere whose humidity is to be measured. The information on the atmospheric temperature (t) take-in by the temperature sensor 23 is received into a microprocessor 24 where it is digitally converted. The humidity detecting element 7 and a resistance 22 are connected in series and supplied with a D.C. voltage from a power source. The resistance 22 does not have a temperature compensating function as the previously described reference element has. Therefore, the voltages at the opposite ends of the resistance 22 exhibit a temperature dependence. This temperature dependent portion can be approximated by the following general equation for the temperature resistance characteristic of a platinum temperature detector which will be described hereinbelow.

$$Rt = Ro(1 + \alpha t - \beta t^2)$$

The constants Ro, $\alpha$ and $\beta$ are previously stored in the memory of the microprocessor 24, and Rt is calculated from the atmosphere temperature (t) provided by the temperature sensor 23 and added or subtracted by a temperature dependent portion from the data taken-in from the resistance 22, thus giving the data of a humidity. The various calculations are made on the basis of the data on the temperature and the humidity to give indicating data of an absolute humidity, a relative humidity, a dew point, specific humidity, etc.

A humidity control device can be realized by the comparison of the above-described calculation results and a desired control value.

It can be understood by those skilled in the art that various modification for the embodiment which has been described in detail can be made within the scope of the present invention.

For the heat resistance wire coil of the humidity detecting element and the reference element, the example of the platinum wire has been given. In the present invention, such a coil is used not only as a resistance wire for maintaining the element at a constant temperature but also for detecting both of a heat conduction and an electric conduction and hence, a metal wire or noble metal alloy wire (e.g., platinum or platinum/iridium wire) having a temperature-resistance characteristic and which is difficult to oxidize at a higher temperature is required to provide a larger output.

In the measuring circuit shown in FIG. 2, the reference element 8 has been sealed in the dry air with a dew point of about $-45°$ C. and with a saturated absolute humidity of about $0.1$ g/m$^3$ which value is considered as a standard condition, and the deviation from such value has been measured, but the humidity in the atmosphere in which the reference element 8 is disposed may be set at any value, so that the deviation from such set value can be measured.

In addition, it is apparent that if the output from the bridge circuit shown in FIG. 2 is connected to a voltmeter or ammeter, the deviation in humidity can be measured, and an absolute humidity meter, a relative humidity meter, a dew-point meter, specific humidity meter and the like can be realized by the functional calculation of a signal from the temperature detector for detecting the open air temperature.

Further, if a voltage comparator is provided in the output of the bridge circuit or at a suitable point in the above meters, a humidity control device can readily be realized.

TABLE 1

| Sample No. | Weight Ratio | | | | | Output (mV) |
|---|---|---|---|---|---|---|
| | Al$_2$O$_3$ | SnO$_2$ | ZnO | TiO$_2$ | MgO | |
| 1 | 1 | 0 | 0 | 1 | 0 | 20.4 |
| 2 | 1 | 0 | 0 | 0 | 1 | 24.0 |
| 3 | 1 | 1 | 0 | 0 | 0 | 20.8 |
| 4 | 1 | 1 | 0 | 1 | 0 | 20.0 |
| 5 | 2 | 1 | 0 | 0 | 1 | 31.6 |
| 6 | 1 | 2 | 0 | 0 | 1 | 29.4 |
| 7 | 1 | 1 | 1 | 1 | 1 | 20.0 |
| 8 | 1 | 0 | 1 | 0 | 0 | 16.0 |
| 9 | 1 | 0 | 1 | 1 | 0 | 18.0 |
| 10 | 2 | 0 | 1 | 0 | 1 | 24.4 |
| 11 | 1 | 0 | 2 | 0 | 1 | 17.6 |
| 12 | 1 | 1 | 1 | 0 | 0 | 25.0 |
| 13* | 1 | 0 | 0 | 0 | 0 | 22.0 |
| 14** | 0 | 0 | 0 | 0 | 0 | 25.5 |

*Sample No. 13 is produced by sintering only Al$_2$O$_3$ to a heating resistance wire coil.
**Sample No. 14 is only a heating resistance wire coil and corresponds to the conventional platinum wire humidity sensing element.

What is claimed is:

1. A humidity detector, comprising:
a humidity sensing element having a heating resistance wire coil having exposed opposite ends and a humidity sensing portion of a metal oxide or metal oxides sintered on said coil and porous to water vapor between said opposite ends;
heating means for energizing said coil to increase the temperature of the humidity sensing portion to a level higher than the temperature in a measuring atmosphere; and
resistance variation detecting means for detecting the variation in resistance between the opposite ends of said coil depending upon the humidity contained in the measuring atmosphere.

2. A humidity detector according to claim 1, wherein said metal oxide is Al$_2$O$_3$ or a mixture of Al$_2$O$_3$ with at least one selected from the group consisting of SnO$_2$, ZnO, TiO$_2$ and MgO.

3. A humidity detector according to claim 1, wherein said heat resistance wire coil is made of a metal or noble metal alloy wire which is oxidation resistant and whose resistance varies with temperature.

4. A humidity detector according to claim 1, wherein said humidity detecting element is heated by energization in a measuring atmosphere, so that molecules of water in the humidity sensing portions are dissociated to supply protons, thereby forming an electrolyte layer to provide an increase in electric conductivity of the humidity sensing portion.

5. A humidity detector according to claim 1, wherein said humidity detecting element is heated by energization in a measuring atmosphere to a temperature as high as 400° C. and operated at this temperature.

6. A humidity detector according to claim 1, wherein said heating means and said resistance variation detecting means includes a bridge circuit having said humidity sensing element therein and including a reference element identical in type with said humidity detecting element disposed in an atmosphere having known humidity, and a power source.

7. A humidity detector according to claim 1, wherein said resistance variation detecting means is a microprocessor for calculating the variation in resistance depending upon the humidity, from the output under the influence of the atmosphere temperature of said humidity detecting element disposed in the measuring atmosphere and the output of a temperature sensor for the atmosphere temperature.

* * * * *